United States Patent
Islava

[19]

[11] Patent Number: 5,829,430
[45] Date of Patent: Nov. 3, 1998

[54] ENDOTRACHEAL TUBE HOLDER

[76] Inventor: Steven T. Islava, 315 Marigold, Corona Del Mar, Calif. 92625

[21] Appl. No.: 785,387

[22] Filed: Jan. 21, 1997

[51] Int. Cl.⁶ .................................................. A61M 16/00
[52] U.S. Cl. .............................. 128/200.26; 128/201.14; 128/912; 128/DIG. 26
[58] Field of Search ......................... 128/200.26, 207.17, 128/207.18, 207.14, 207.15, 911, 912, DIG. 26

[56] References Cited

U.S. PATENT DOCUMENTS

| | | | |
|---|---|---|---|
| 3,774,616 | 11/1973 | White et al. .................... | 128/200.26 |
| 3,924,636 | 12/1975 | Addison ......................... | 128/DIG. 26 |
| 3,946,742 | 3/1976 | Eross ............................. | 128/DIG. 26 |
| 4,069,820 | 1/1978 | Berman . | |
| 4,270,529 | 6/1981 | Muto .............................. | 128/200.26 |
| 4,331,143 | 5/1982 | Foster ............................ | 128/207.17 |
| 4,744,358 | 5/1988 | McGinnis ...................... | 128/DIG. 26 |
| 4,832,020 | 5/1989 | Augustine ...................... | 128/207.14 |
| 5,024,218 | 6/1991 | Orassapian et al. ........... | 128/200.26 |
| 5,069,206 | 12/1991 | Crosbie .......................... | 128/207.17 |
| 5,306,233 | 4/1994 | Glover ........................... | 128/207.17 |
| 5,402,776 | 4/1995 | Islava ............................ | 128/207.17 |
| 5,437,273 | 8/1995 | Bates et al. ................... | 128/207.17 |
| 5,490,504 | 2/1996 | Vrona et al. .................. | 128/912 |
| 5,513,633 | 5/1996 | Islava ............................ | 128/207.17 |

*Primary Examiner*—John G. Weiss
*Assistant Examiner*—V. Srivarstava
*Attorney, Agent, or Firm*—Harold L. Jackson

[57] ABSTRACT

An endotracheal tube holder secures an endotracheal tube in a selected position within the patient's mouth and trachea and includes a tube holding block having an elongated cradle that extends inwardly of a patient's mouth. The holding block is formed having a tube clasp housing in which is located a plurality of tube securing pins, whereby the endotracheal tube is held in place by the securing pins and a pair of oppositely disposed flexible flange members which engage and hold the tube in a substantially fixed position with respect to the patient's mouth, and wherein a flexible biting block is interposed between the tube cradle and the tube clasp housing.

15 Claims, 2 Drawing Sheets

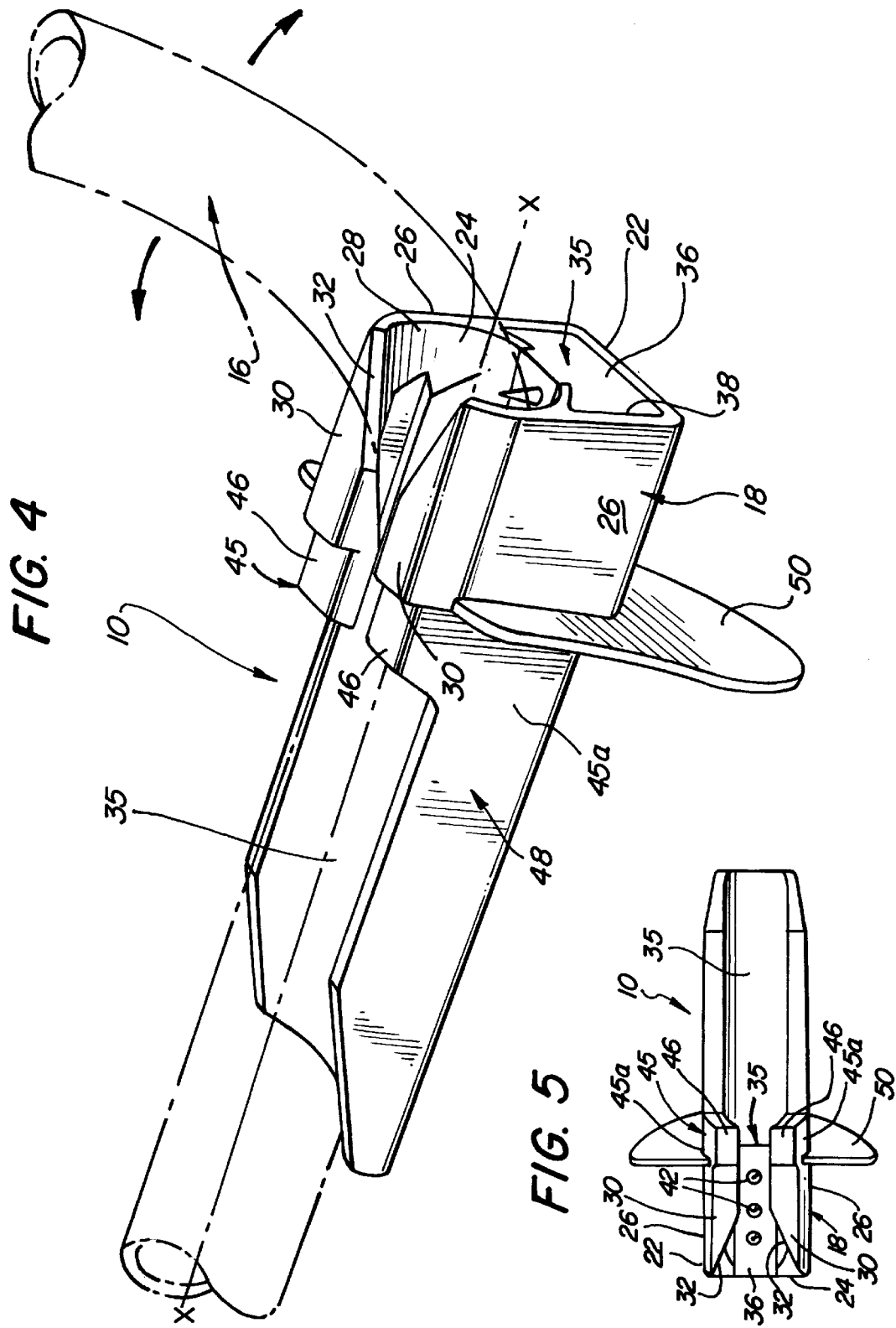

ENDOTRACHEAL TUBE HOLDER

BACKGROUND OF THE INVENTION

1. Field of the Invention

The present invention relates generally to an endotracheal tube holding device and more particularly to an endotracheal tube holder in which an endotracheal tube is secured after the tube has been inserted and correctly positioned within the patient's mouth and trachea.

2. Description of the Prior Art

Endotracheal tubes are used under several conditions such as in the ventilation of a patient during anesthesia and resuscitation, as well as during critical care that commonly arises not only in the hospital but also while a patient is being transported.

There is a need in the art to provide a suitable means for securing an endotracheal tube by a simple but positive arrangement of a small mouthpiece that includes an attachable faceplate.

Many types of endotracheal tube holder arrangements, using securing devices, have been tried in the prior art. These often included simply mounting the tube in place with adhesive tape that was applied to the tube and several areas of the patient's face. Some endotracheal tubes were mounted in a faceplate that included a bite block whereby the patient was required to grip the bite block with his or her teeth. However, other prior art tube holders have included locking means for securing the endotracheal tube to the faceplate of the tube holder.

For typical examples of prior art endotracheal tube holders one may refer to those disclosed in the following U.S. Patents:

U.S. Pat. No. 3,946,742 reissued to Bela Eross
U.S. Pat. No. 4,069,820 issued to R. A. Berman
U.S. Pat. No. 4,270,529 issued to R. Muto
U.S. Pat. No. 4,331,143 issued to B. R. Foster
U.S. Pat. No. 4,832,020 issued to S. D. Augustine
U.S. Pat. No. 5,024,218 issued to Andranik Ovassapian, et al.
U.S. Pat. No. 5,069,206 issued to David B. Crosbie
U.S. Pat. No. 5,306,233 issued to David F. Glover
U.S. Pat. No. 5,402,776 issued to Steve Islava
U.S. Pat. No. 5,437,273 issued to D. A. Bates
U.S. Pat. No. 5,513,633 issued to Steve T. Islava

BRIEF SUMMARY AND OBJECTS OF THE INVENTION

The present invention, which defines an endotracheal tube holder that secures the tube in a selected position within the patient's mouth and trachea, comprises a tube holding block defined by an elongated body member extending inward of patient's mouth to define a tube cradle. The outer extended portion of the holding block is formed having a tube clasp housing, in which is located a tube securing means. The endotracheal tube is held in place by a tube securing means, including a pair of oppositely disposed flexible flange members that form an integral part of the tube clasp housing which secures the tube in a substantially fixed position with respect to the patient's mouth. Preferably, the tube securing means further includes a plurality of pin members which engage the wall of the tube positioned opposite the flange members. A flexible biting block, formed as an integral part of the holder, is interposed between the tube cradle and the tube clasp housing. The endotracheal tube is adjustably positioned in the patient's mouth, after which the tube clasp is easily positioned about the endotracheal tube so that a faceplate mounted to the housing engages the lips and adjacent area of the patient, at which time an adhesive face band carried by the faceplate is secured to the area surrounding the patient's mouth. Once the face plate is secured to the patient's face, the tube is snapped into the tube clasp housing and will remain in place in its installed position.

Thus, the present invention has for an important object to provide a simple but unique endotracheal tube holder that includes a holding block which includes a tube cradle and a tube clasp housing, the housing having a faceplate on which an adhesive faceband is mounted, whereby the holding device is secured to the patient's face.

Another object of the invention is to provide an endotracheal tube holder that is arranged to be attached to the endotracheal tube after the tube has been inserted and correctly positioned in the patient's mouth and trachea.

Still another object of the present invention is to provide a tube holder that includes a positive tube holding means that is integrally formed with a tube cradle that supports the tube inside the patient's mouth and over the tongue.

Yet another object of the present invention is to provide an endotracheal tube holder that will accommodate a number of different sizes of tubes, whereby a selected tube can be firmly secured within the housing of the tube holding block.

Still another object of the invention is to provide an endotracheal tube clasp or holder that includes a bite-block having a pair of pressure clamping flanges that hold the tube in engagement with a plurality of securing pins located in the housing.

A still further object of the invention is to provide a tube clasp or holder of this character that is simple in construction and relatively inexpensive to manufacture.

The characteristics and advantages of the invention may best be understood by reference to the following description taken in connection with the accompanying drawings, where like components are given the same reference numerals. After considering the preferred embodiment described herein, skilled persons will understand that variations may be made without departing from the principles disclosed; and I contemplate the employment of any structures, arrangements or modes of operation that are properly within the scope of the appended claims.

BRIEF DESCRIPTION OF THE DRAWINGS

FIG. 4 is a perspective view of the present invention with an endotracheal tube in phantom lines and mounted therein; and FIG. 5 is a top plan view thereof.

DETAILED DESCRIPTION OF THE INVENTION

Figure 1:
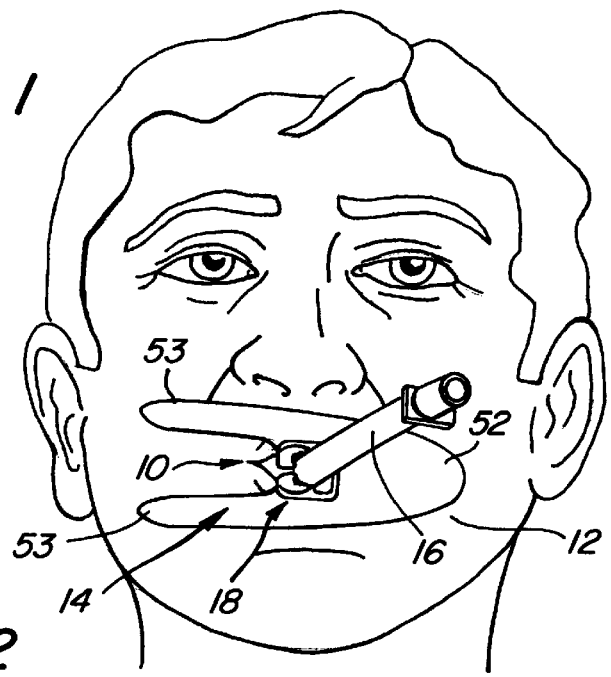
FIG. 1 is a pictorial view of an endotracheal tube clasp or holder that illustrates the present invention mounted in an operative position as worn by a patient.

Referring more particularly to FIG. 1, there is shown the preferred embodiment of the present invention defined as an endotracheal tube holder, generally indicated at 10, which is securely mounted to the patient's face 12 by an attaching means defined by an adhesive faceband 14.

The endotracheal tube holder 10 is adapted to be mounted to an endotracheal tube 16 after it has been inserted and positioned within the patient's mouth and trachea. The present invention is particularly designed to be readily mounted and attached to the endotracheal tube as will be hereinafter disclosed.

Figure 2:
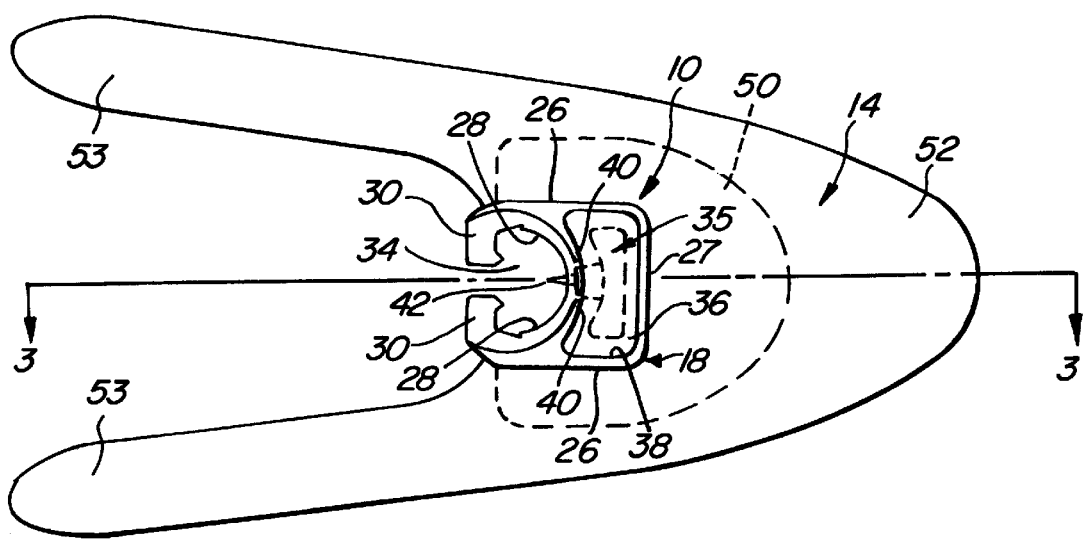
FIG. 2 is a front-elevational view of the endotracheal tube clasp.

The endotracheal tube holder 10 comprises a tube holding block, indicated generally at 18. See FIGS. 2 through 5. The tube holding block 18 has a longitudinal axis x-x and includes an integrally formed tube clasp housing 22. The housing 22 has an open receiving end 24 defined by side walls 26 which are formed having an upper arcuate inner surface 28, wherein each wall terminates at its upper end to define a pair of inwardly extending flexible flange members 30. These flexible flange members are shaped with diverging edges 32 (FIG. 3) so as to provide and define the open receiving end 24, whereby these edges 32 are arranged to allow an endotracheal tube 32 to be positioned in the longitudinal passage 34 (FIGS. 2 and 3) defined by side walls 26 so as to be secured within passage 34 for engagement with the flexible flange members 30, as illustrated in FIG. 4. The flange members move outwardly to allow the tube to be snapped into place and then exert a downward pressure against tube 32 and force the lower wall of the tube into engagement with a tube grasping member indicated generally at 35. The tube grasping element includes a pin support member 36 adapted and formed to be positioned in a recess 38 defined by side walls 26, bottom wall 27, and by a pair of oppositely disposed arcuate members 40 integrally formed as part of the respective side walls 26. See FIGS. 3 and 4. A plurality of pins 42 are fixedly mounted in the pin support member 30 define an elongated opening therebetween which is narrower than the diameter of the tube to be inserted into the passage as is illustrated in FIG. 1. The flange members 36 and are arranged to engage the outer surface of the lower wall of the tube 16, thus preventing tube 16 from sliding within passage 34. The flexible flange members 30 and the tube grasping member 36, 42 are sometimes referred hereinafter as the tube securing means.

Figure 3:
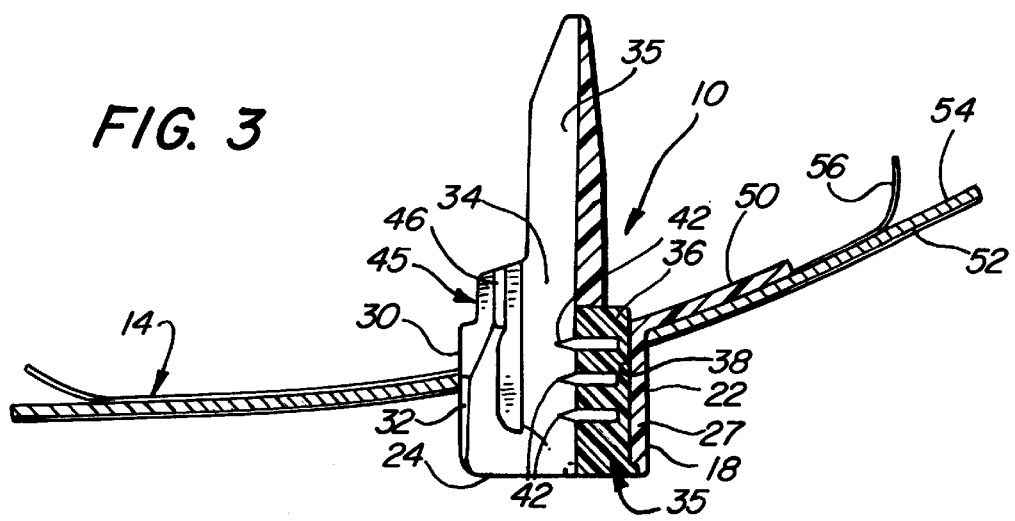
FIG. 3 is a cross-sectional view of the endotracheal tube clasp taken substantially along line 3—3 of FIG. 2.

A bite block, generally designated at 45, is formed as an integral part of tube holding block 18 and is defined by a pair of side walls 45a forming a rearward extension of side walls 26 and a second pair of stepped down flange members 46 integrally formed with flexible flange members 30. The flange members 46 also serve to force the tube against the pins 42 in response to a patient's biting action. The tube holding block further includes an integrally formed tube cradle 48 in which the endotracheal tube is adapted to rest when secured within passage 34, as illustrated in FIGS. 3, 4 and 5. The cradle provides a rearward extending U-shaped channel 35 which is an extension of the passageway 34.

A faceplate 50 is also formed as an integral part of the tube clasp housing 22 and extends outwardly from side walls 26 and bottom wall 27 so as to engage the patient's mouth. The faceplate also provides a means for mounting the adhesive faceband 14, as illustrated in FIG. 1. The adhesive faceband 14 comprises a flexible curved thin support member 52 and a pair of thin elongated strips 53 that extend across the mouth area of the patient. The inner surface 54 of the faceband is coated with an adhesive which is generally covered with a removable release sheet 56, such as paper, which is removed when the endotracheal tube clasp is ready for use.

The tube holding block 18 is preferably molded from a thermoplastic elastomer such as polyethylene. The pin support member 36 is preferably made of a rigid material such as a rigid plastic or stainless steel. The pins 42 are preferably made of stainless steel. The pin support member 36 may be secured within the recess 38 of the holding block 18 by means of a suitable adhesive.

The foregoing should only be considered as illustrative of the principles of the invention. Further, since numerous modifications and changes may readily occur to those skilled in the art, it is not desired to limit the invention to the exact construction and operation as shown and described, and accordingly, all suitable modifications and equivalents may be resorted to, falling within the scope of the claimed invention.

What is claimed is:

1. In combination an endotracheal tube and an endotracheal tube holder adapted to be secured to the endotracheal tube after the tube has been correctly positioned within the patient's mouth and trachea, the combination comprising:

an endotracheal tube;

a holding block;

a tube clasp housing formed in the holding block having a longitudinal axis, a lower wall and a pair of side walls forming a longitudinal passageway for receiving the endotracheal tube, the side walls having inwardly extending flexible upper ends defining an elongated opening therebetween which is narrower than the diameter of the tube for receiving the tube;

a tube grasping member positioned within the lower portion of the tube clasp housing opposite the flexible upper ends of the side walls, the flexible upper ends exerting a downward pressure against a tube positioned within the passageway to force the tube into an engagement with the tube grasping member to secure the tube in a fixed longitudinal position within the housing;

an elongated tube cradle integrally formed with the tube clasp housing so as to extend rearwardly along the longitudinal axis, whereby the endotracheal tube is supported in the tube cradle;

a bite block interposed between the tube cradle and the tube clasp housing, the bite block having a pair of side walls extending parallel to and rearwardly of the housing side walls, the bite block side walls being arranged to engage the patient's teeth;

a faceplate formed on the tube clasp housing and positioned to engage the mouth of the patient and prevent inward movement of the tube holder;

a faceband mounted to the faceplate and arranged to be secured to the face of the patient; and means for removably affixing the faceplate to the face of a patient whereby the tube cradle and bite block may be inserted into a patient's mouth with the face plate positioned against the area surrounding a patient's mouth and the tube snapped sideways into the tube clasp housing and retained therein.

2. The combination as recited in claim 1, wherein the upper ends of the side walls of the tube clasp housing are in the form of inwardly extending flange members integrally formed with the side walls and arranged to force the endotracheal tube into engagement with the tube grasping member to secure the tube in a fixed position within the clasp housing.

3. The combination as recited in claim 2, wherein the tube clasp housing is further formed having a recess positioned below the longitudinal, passage, wherein the tube grasping member is fixedly mounted within the longitudinal passageway.

4. The combination as recited in claim 3, wherein the tube grasping member comprises a pin support member having a plurality of pin members protruding outwardly therefrom so as to extend into the longitudinal passageway for engagement with the surface of the endotracheal tube.

5. The combination as recited in claim 4, wherein the bite block includes a second pair of inwardly extending flange members that are integrally formed with the flexible flange members of the tube clasp housing and extend inwardly therefrom, thereby permitting the patient to bite down on the bite block so as to clasp the endotracheal tube between the flange members and the pins, thereby securing the endotracheal tube in place.

6. The combination as recited in claim 5, wherein the elongated tube cradle is formed having a U-shaped channel interconnected with the longitudinal passageway.

7. The combination as recited in claim 6, wherein the faceband is formed having a support member and a pair of elongated strip members that are arranged to extend across the mouth area of the patient, wherein the contacting surface of the faceband is coated with an adhesive for removably mounting the faceband to the patient's face.

8. An endotracheal tube holder arranged to be securely mounted on an endotracheal tube after the tube is inserted and correctly positioned within a patient's mouth and trachea, the holder comprising:

a holding block having a longitudinal axis;

a tube clasp housing formed in the holding block, the housing having an open tube receiving end, a pair of side walls, a bottom wall and a pair of flexible flange members integrally formed with and extending inwardly from the upper ends of the side walls and a tube grasping surface positioned below and opposite the flange members, the side walls defining a longitudinal passage for receiving the tube; the flange members defining an elongated opening therebetween which is narrower than the diameter of the tube, the flange members being arranged to flex outwardly to permit entry of the tube into the longitudinal passage, the flange members exerting a downward pressure on an endotracheal tube positioned in the passage to force the tube against the tube grasping surface to secure the tube in a fixed position within the housing;

a bite block formed integrally with the housing and having a pair of side walls extending parallel to and rearwardly from the housing side walls, the bite block side walls being arranged to engage the teeth of a patient;

an elongated generally U-shaped tube cradle extending rearwardly along the longitudinal axis of the bite block for receiving the endotracheal tube;

a face plate formed on the housing and arranged to contact the area surrounding a patient's mouth to prevent inward movement of the tube holder;

a face band mounted to the faceplate, and means for removably affixing the faceplate to the face of a patient whereby once the endotracheal tube has been properly positioned in a patient's trachea, the U-shaped tube cradle and bite block portion of the endotracheal tube holder may be inserted into a patient's mouth with the face plate positioned against the area surrounding a patient's mouth and the tube snapped sideways into the tube clasp housing and retained therein.

9. The endotracheal tube holder of claim 8 wherein the flexible flange members of the housing are arranged to force the endotracheal tube against the bottom wall of the housing.

10. The endotracheal tube holder of claim 9 further including tube grasping means positioned on the inner surface of the bottom wall of the housing for engaging the outer surface of the tube.

11. The endotracheal tube holder of claim 10 wherein the flexible flange members of the housing have edges which diverge in a direction away from the bite block.

12. An endotracheal tube holder as recited in claim 10, wherein the tube grasping means comprises a pin support member having a plurality of pin members protruding outwardly therefrom so as to extend into the longitudinal passage for engagement with the outer surface of the endotracheal tube.

13. An endotracheal tube clasp assembly as recited in claim 12, wherein the bite block includes a second pair of flange members that are integrally formed with the flexible flange members of the tube clasp housing and extend inwardly therefrom, thereby permitting the patient to bite down on the bite block so as to clasp the endotracheal tube between the flange members and the pins of the securing means.

14. An endotracheal tube holder as recited in claim 13, wherein the elongated tube cradle is formed having a U-shaped channel interconnected to the longitudinal passage.

15. An endotracheal tube clasp assembly as recited in claim 14, wherein the faceband is formed having a support member and a pair of elongated strip members that are arranged to extend across the mouth area of the patient, wherein the contacting surface of the faceband is coated with an adhesive for removably mounting the faceband to the patient's face.

* * * * *